United States Patent
Hatcher et al.

(10) Patent No.: US 6,867,586 B2
(45) Date of Patent: Mar. 15, 2005

(54) EDDY CURRENT INSPECTION PROBE FOR INSPECTING MULTIPLE PORTIONS OF A TURBINE BLADE HAVING DIFFERENT GEOMETRIC SURFACES

(75) Inventors: Clifford Hatcher, Pittsburgh, PA (US); Robert Echols, Kingwood, TX (US)

(73) Assignee: Siemens Westinghouse Power Corporation, Orlando, FL (US)

( * ) Notice: Subject to any disclaimer, the term of this patent is extended or adjusted under 35 U.S.C. 154(b) by 17 days.

(21) Appl. No.: 10/245,423

(22) Filed: Sep. 17, 2002

(65) Prior Publication Data

US 2004/0051525 A1 Mar. 18, 2004

(51) Int. Cl.[7] .......................... G01N 27/72; G01R 33/12
(52) U.S. Cl. ...................... 324/239; 324/262; 324/240
(58) Field of Search ................. 324/239, 219, 324/226, 237, 238, 240, 262

(56) References Cited

U.S. PATENT DOCUMENTS 4,139,822 A * 2/1979 Urich et al. ................. 324/219
5,834,937 A * 11/1998 Burris ......................... 324/219
6,036,636 A * 3/2000 Motoki et al. ............... 600/146

OTHER PUBLICATIONS

E. Paul Degarmo et al., "Materials and Processes in Manufacturing", 7th Edition, (1988), pp. 277–279, Macmillan Publishing Company, NY, USA.

* cited by examiner

Primary Examiner—Jay Patidar

(57) ABSTRACT

An eddy current inspection probe provides multiple interchangeable configurations for enabling an inspector to reach most or all portions of most or all turbine blades within a combustion turbine by inserting the probe through an inspection port, without disassembling the turbine. The probe shaft contains the electronic signal wire for the inspection tip and a port for a video probe, thereby facilitating use of the video probe and protecting these components. The inspection tip connector at the end of the main shaft is pivotally secured to the shaft, and may be set at any desired angle by using a semirigid or rigid member passing through the shaft, and connected to lever within the handle. Any one of a plurality of probe tips and shaft extensions may be selected to configure the inspection probe to reach a desired location within the turbine.

20 Claims, 5 Drawing Sheets

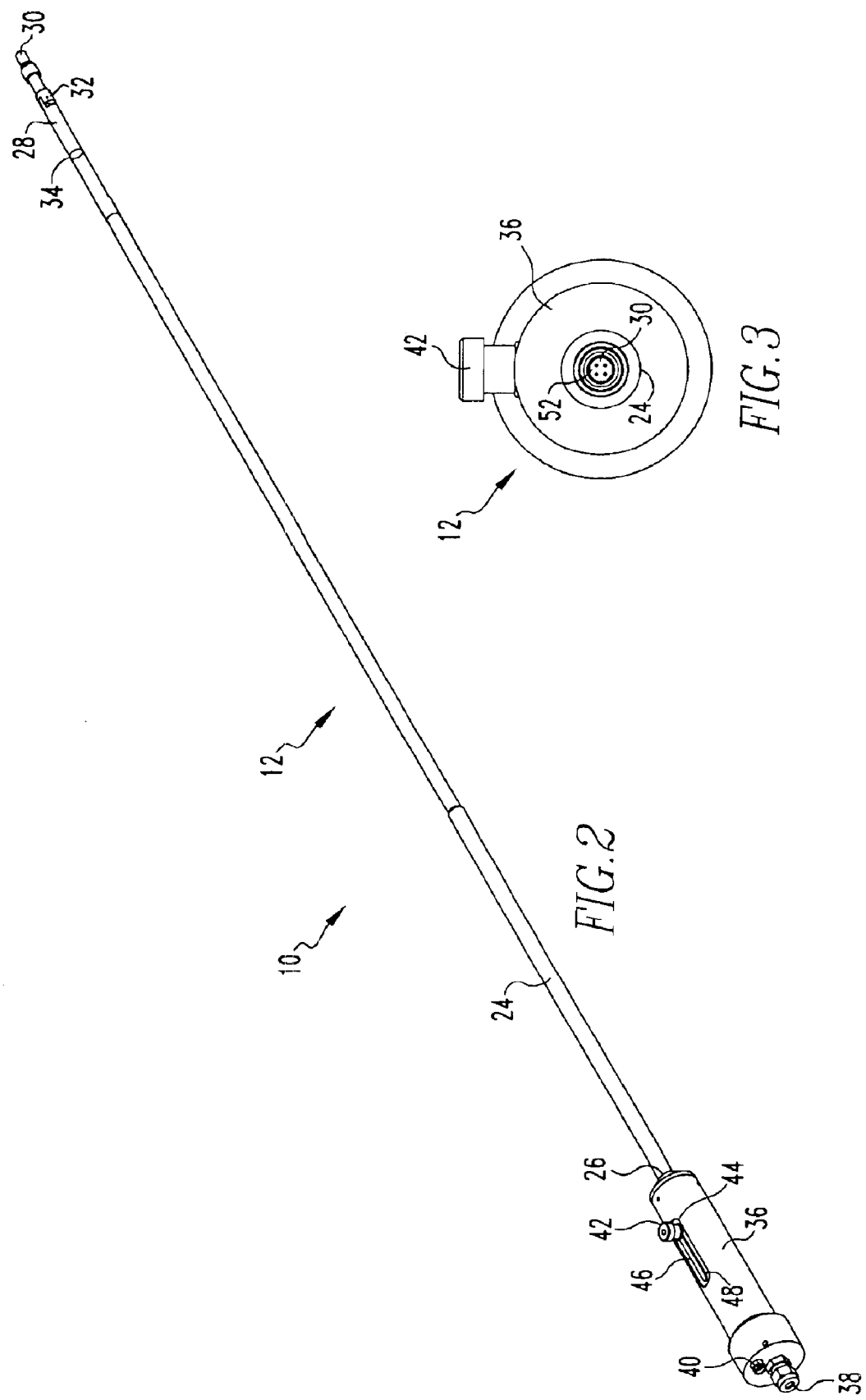

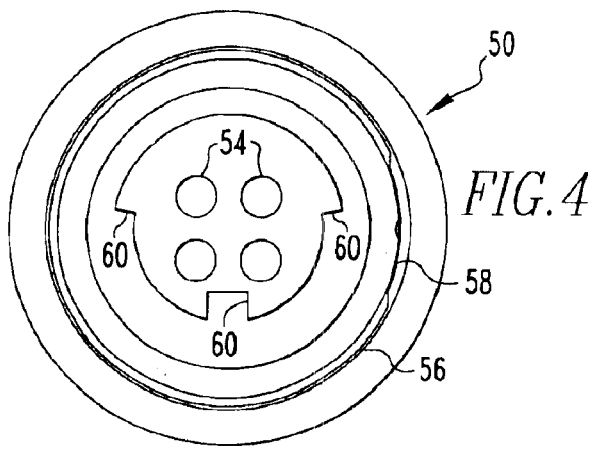
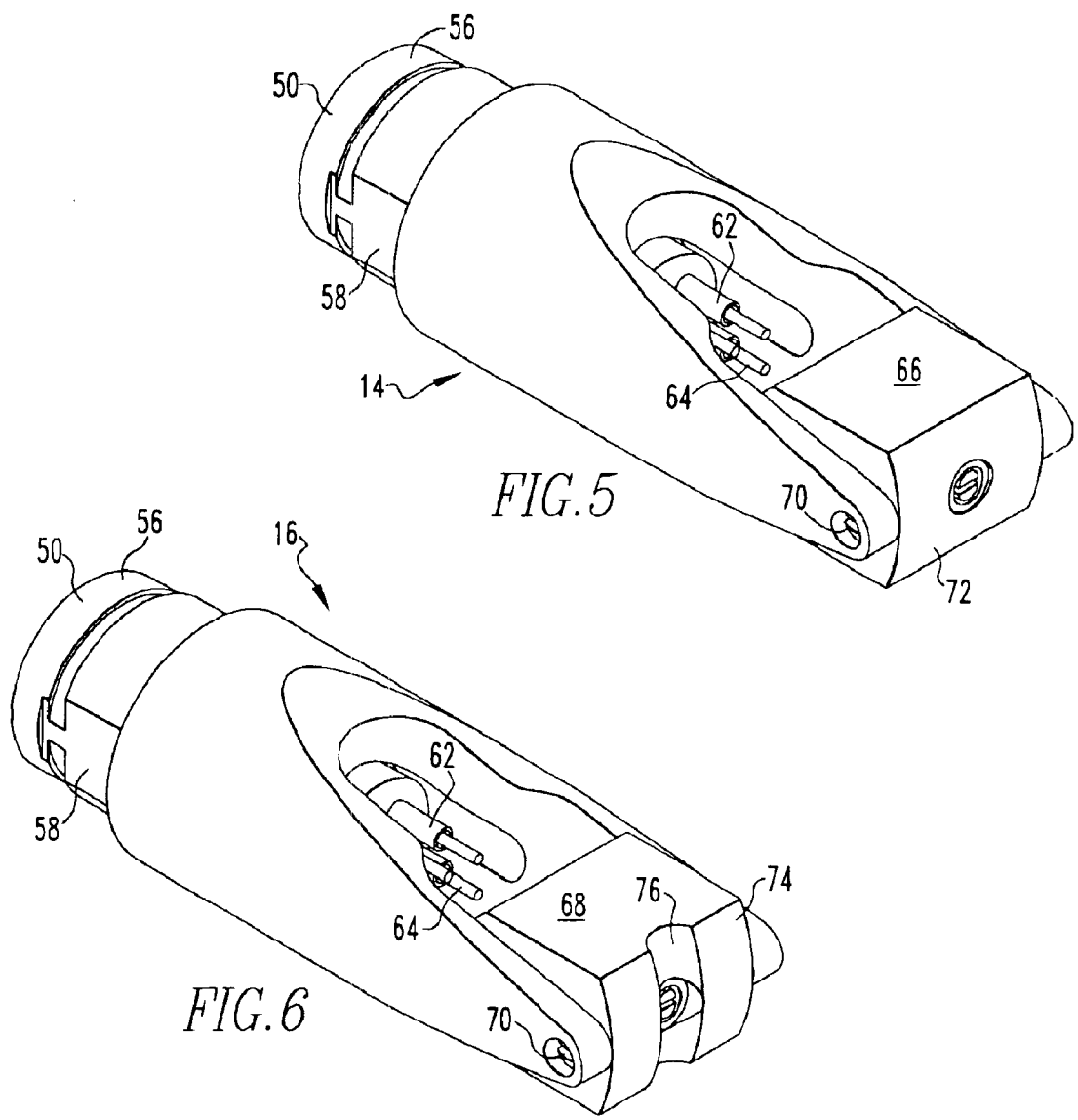

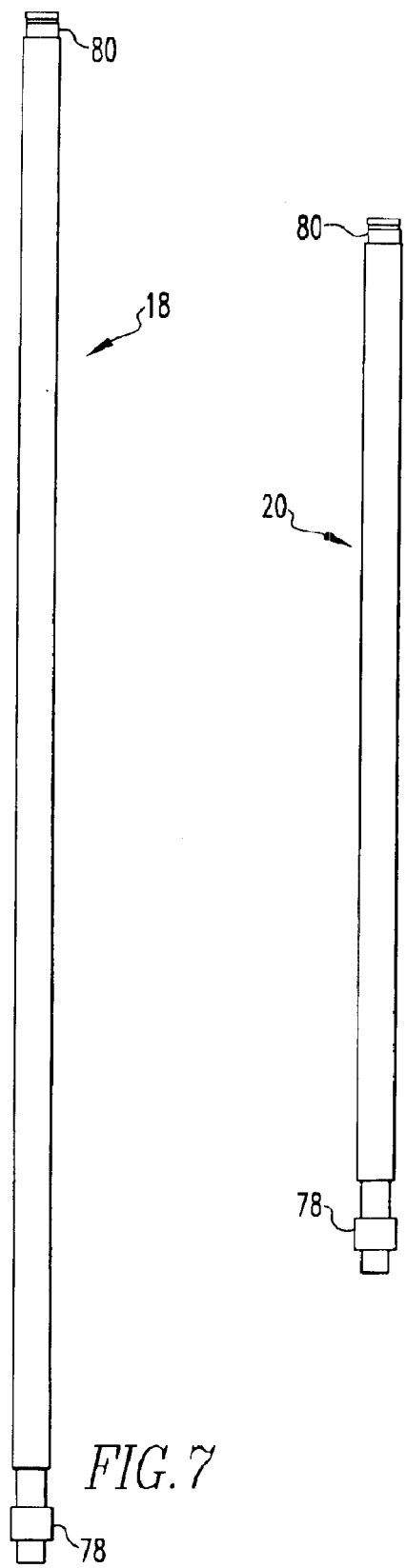
FIG.7  FIG.8
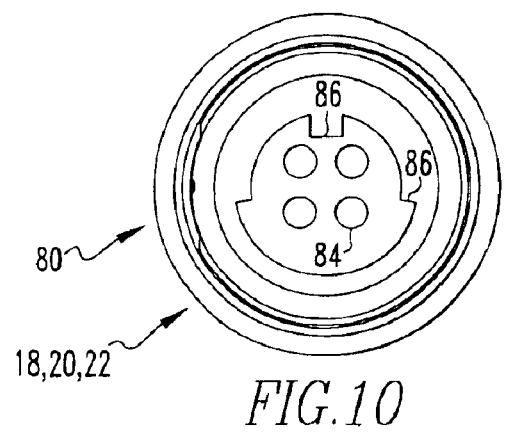
FIG.10
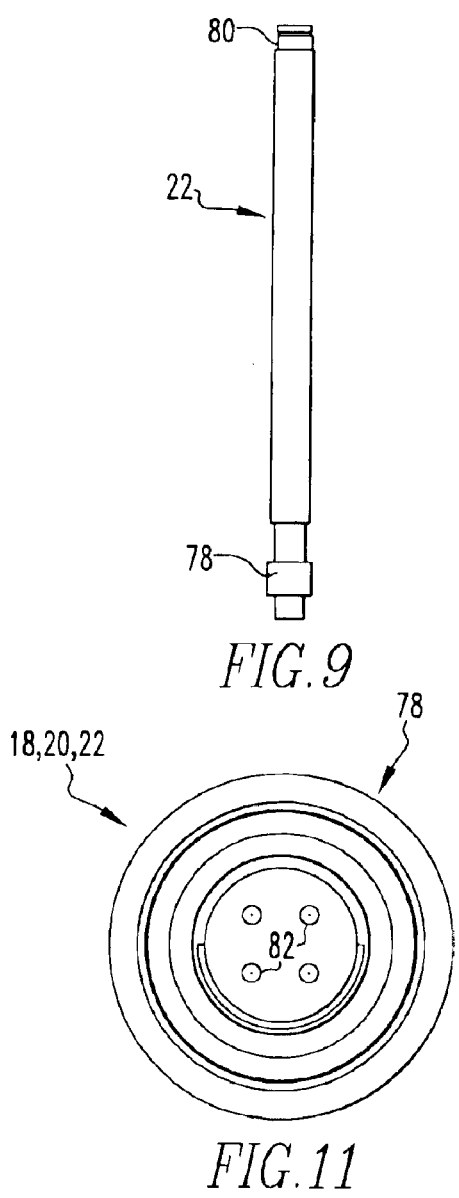
FIG.9
FIG.11

EDDY CURRENT INSPECTION PROBE FOR INSPECTING MULTIPLE PORTIONS OF A TURBINE BLADE HAVING DIFFERENT GEOMETRIC SURFACES

BACKGROUND OF THE INVENTION

1. Field of the Invention

The present invention provides an improved eddy current probe that is particularly useful for inspecting the interior of a combustion turbine without disassembly of the turbine.

2. Description of the Related Art

Eddy current testing of electrically conductive material is typically performed by exposing the material to an alternating magnetic field generated by a coil carrying an alternating current. The magnetic field generates small electric currents at or near the surface of the material, commonly known as eddy currents. The eddy currents generate their own magnetic fields, which, when they interact with the magnetic field of the exciting coil, will change the electrical impedance of the coil. The impedance of the exciting coil may be measured, and is compared with the impedance of a separate indicating coil, thereby detecting any condition that would affect the conductivity of the test material. Such conditions include cracks, voids, inclusions, seams, and stress concentrations at or near the surface of the material. Additionally, differences in metal chemistry and/or heat treatment of the metal will affect the conductivity and magnetic permeability of the test material, and may therefore be detected by eddy current inspection. The thickness of platings, coatings, and/or corrosion also lend themselves to eddy current measurements.

An eddy current inspection system includes a coil contained within a probe, for carrying alternating currents and inducing eddy currents in the part being tested; a coil for sensing the magnetic field changes caused by the interaction of the eddy currents with the original magnetic field, which may be either the exciting coil or a separate sensing coil; and a means of measuring and interpreting the resulting impedance changes, for example, measuring the induced voltage of the sending coil. Different types of eddy current probes include absolute coils, which consist of a single winding where the impedance or induced voltage in the coil is measured directly; a differential coil, which utilizes a pair of opposing coils, and compares the change in inductance within one coil to the change in inductance within the other coil; and torroid coils, which directly monitor the driving coil and measures changes in the impedance of the coil due to changes in conductivity and permeability.

The inaccessibility and small size of the open space within the combustion turbine, and between and among the turbine blades, makes inspection of the blades difficult without partial disassembly of the turbine. Presently available eddy current probes, configured for insertion through the inspection ports on the turbine, are unable to reach all portions of a blade within the turbine that need to be inspected. Additionally, it is difficult to determine the exact location of such probes within the turbine, thereby creating a possibility that certain regions that need to be inspected will be missed during the inspection.

Accordingly, there is a need for an eddy current probe that is adapted to reach all areas of a blade within a turbine through an inspection port. Additionally, there is a need for an eddy current inspection probe tip configured for inspecting different portions of the blade having different geometric shapes. Furthermore, there is a need for an eddy current probe that facilitates precise determination of its location within the turbine.

SUMMARY OF THE INVENTION

The present invention provides an eddy current probe adapted for reaching most or all areas of a blade within the turbine portion of a combustion turbine, by being inserted through an insertion port within the turbine while the turbine is fully assembled.

The eddy current measuring system of the present invention includes a probe shaft, a plurality of shaft extensions and eddy current measuring tips for use in conjunction with the probe shaft, and a display screen for displaying the measured results.

The probe shaft includes an elongated shaft body having a handle at one end and a hingedly secured tip connector at the other end. The main body portion is hollow, containing the electrical wiring for the probe tip and for a video camera mounted in close proximity to the hinge connecting the main body to the tip connector. The main body also contains a semirigid or rigid elongated member extending between the tip connector and a slideably mounted lever contained within the handle, thereby permitting the angle of the tip connector with respect to the shaft to be controlled by the sliding lever. The handle also includes a connection for a cable carrying signals from the eddy current probe, and a port for insertion of a video probe.

Any one of a plurality of eddy current inspection tips may be connected to the shaft, either directly to the tip connector or to a shaft extension which is in turn connected to the tip connector. By selecting a shaft extension of an appropriate length, and controlling the angle of the tip with respect to the shaft from the handle, the probe tip may be positioned to inspect most or all portions of most or all blades within the turbine.

Any one of several eddy current inspection tips may be selected, depending on the specific surface to be inspected. For example, a bullnose tip may be utilized for inspecting the blade platform and airfoil area. A groove nose eddy current tip may be used to inspect the edges of the blade, including, but not limited to, the trailing edge of the blade. Either the bullnose or groove nose eddy current probe tip may be supplied containing an absolute coil, a differential coil or a torroid coil.

By selecting an appropriate inspection tip, and possibly an appropriate shaft extension, the inspection shaft may be configured to reach most or all portions of the turbine blades through one of the inspection ports provided on a turbine. The video probe permits the inspector to precisely position the probe tip in the location desired, thereby insuring that all surfaces requiring inspection are actually inspected. By housing the electronic signal cables for both the eddy current probe and video camera within the main shaft portion, the risk of damage to these components during inspection of a turbine is minimized. By eliminating the need to disassemble the turbine to perform the inspection, the amount of nonproductive downtime for the turbine is minimized.

BRIEF DESCRIPTION OF THE DRAWINGS

FIG. 2 is an isometric top and side view of an eddy current probe shaft according to the present invention.

FIG. 3 is a tip view of an eddy current probe shaft according to the present invention.

FIG. 4 is a connector end view of an eddy current probe tip according to the present invention.

FIG. 5 is a top and side isometric view of a bullnose eddy current probe tip according to the present invention.

FIG. 6 is an isometric top and side view of a groove nose eddy current probe tip according to the present invention.

FIG. 7 is a side view of an eddy current probe shaft extension according to the present invention.

FIG. 8 is a side view of an alternative eddy current probe shaft extension according to the present invention.

FIG. 9 is a side view of another alternative embodiment of a probe shaft extension according to the present invention.

FIG. 10 is an end view of the probe shaft extensions of FIGS. 6, 7 and 8, showing the end of the extensions to be connected to the shaft.

FIG. 11 is an end view of the probe extensions of FIGS. 6, 7 and 8, illustrating the end to which a probe tip of FIGS. 4 and 5 will be connected.

Like reference characters denote like elements throughout the drawings.

DETAILED DESCRIPTION

Figure 1:
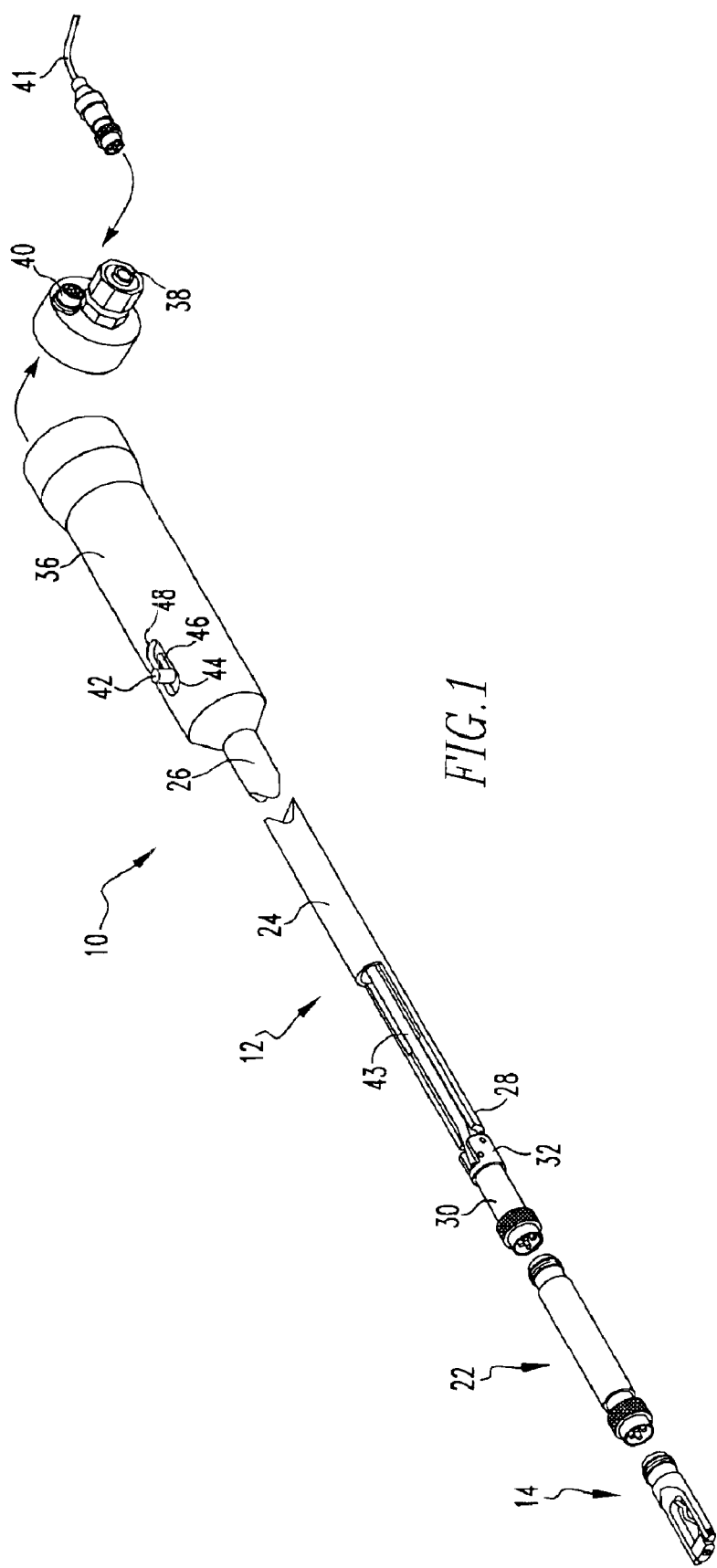
FIG. 1 is a partially cutaway, partially exploded isometric view of an eddy current probe according to the present invention.

The present invention provides an improved eddy current inspection probe that is particularly suitable for accessing most or all blades within the turbine portion of a combustion turbine through an inspection port, without disassembly of the turbine.

Referring to the drawings, the eddy current probe 10 includes a shaft 12, a bullnose tip 14 or groove nose tip 16, and also optionally includes a shaft extension 18, 20, or 22 therebetween.

Referring to FIGS. 1–3, the shaft 12 includes a main shaft body 24 having a handle end 26 and a probe end 28. The probe end 28 includes a tip connector 30, attached to the probe end 28 by the pivot 32. The tip connector 30 and other connectors described herein may be of the threaded collar type. The probe end 28 also preferably includes a video probe 34, located in close proximity to the pivot 32. The handle end 26 is rigidly secured to the handle 36. The handle 36 includes a video probe port 38 and an eddy current probe cable connector 40, providing for an electrical connection to the eddy current cable 41. The handle also includes a sliding lever 42, connected to a semirigid or rigid elongated member 43, for example, a metal strip, passing through the hollow main shaft body 24 alongside the signal cable for the eddy current probe and the video probe, to connect with the pivot 32 of the tip connector 30. Therefore, when the lever 42 is positioned at the end 44 of the slot 46, the tip connector 30 will be oriented substantially coaxial with the shaft body 24. Likewise, when the lever 42 is at the opposite end 48 of the slot 46, the tip connector 30 will be oriented substantially perpendicular to the shaft body 24. Positioning the lever 42 in between the ends 44 and 48 will, of course, position the tip connector 30 at any desired angle between substantially parallel and substantially perpendicular to the main body 24.

Referring to FIGS. 4–6, a bullnose tip 14 (FIGS. 4 and 5) and a groove nose tip 16 (FIGS. 4 and 6) are illustrated. Each of the probe tips 14, 16 includes a connector 50 at one end, dimensioned and configured to mate with the tip connector 30. The illustrated example utilizes a male connector 30 and female connector 50, but these can easily be reversed. The illustrated example connectors 30, 50 are configured for four separate wires, with four wire tips 52 (FIG. 3) defined within the connector 30, and four holes 54 dimensioned and configured to receive the wire tips defined in the connector 50. The connector 50 may include an outer ring 56 defining a flat surface 58, for ensuring proper alignment of the wire tips 52 and holes 54 during connection of a probe tip 14, 16 to the connector 30. Noncircular surfaces 60 within the connector 50 may be provided in addition to, or alternatively to, the flat surface 58. Two coils, 62, 64, are located within a central portion of the tip 14, 16. Each coil 62, 64 is electrically connected to two of the four wires providing alternating current to the probe tip 14, 16. Each of the probe tips 14, 16 includes a magnetically permeable nose 66, 68, secured by the pivot 70, at the end opposite the connector 50. The nose 66,68 is preferably dimensioned and configured to be brought into contact with, and to slide along, the turbine blade during an inspection. The face 72 of the bullnose 66 is preferably slightly convex and generally smooth. The face 74 of the groove nose 68 defines a substantially linear groove 76, but is otherwise slightly convex and substantially smooth in a manner similar to that of the face 72 of the bullnose 66.

FIGS. 7–11 illustrate alternative shaft extensions 18, 20, 22. Each shaft extension 18, 20, 22 is dimensioned and configured to fit between the connector 30 and connector 50, thereby increasing the range of possible distances between the probe tip 14, 16, and the connector 30. Each shaft extension 18, 20, 22 includes a male connector 78 at one end essentially identical to the male connector 30, and a female connector 80 at the other end, essentially identical to the connector 50. The male connector 78 defines a plurality of pins, with four illustrated in the present example, dimensioned and configured to mate with the holes 54 within the connector 50. The female connector 80 includes a plurality of holes, with four illustrated in the present example, corresponding to the pins 52 in the connector 30. Nonlinear surfaces 86 defined within the connector 80 insure that the correct pins 52 are inserted in the correct holes 84 upon the connection of the connector 80 and connector 50. Likewise, the noncircular surfaces 58, 60 within the connector 50 insure that the proper pins 82 are connected with the proper holes 54 when the connector 52 and connector 78 are brought together.

Figure 12:
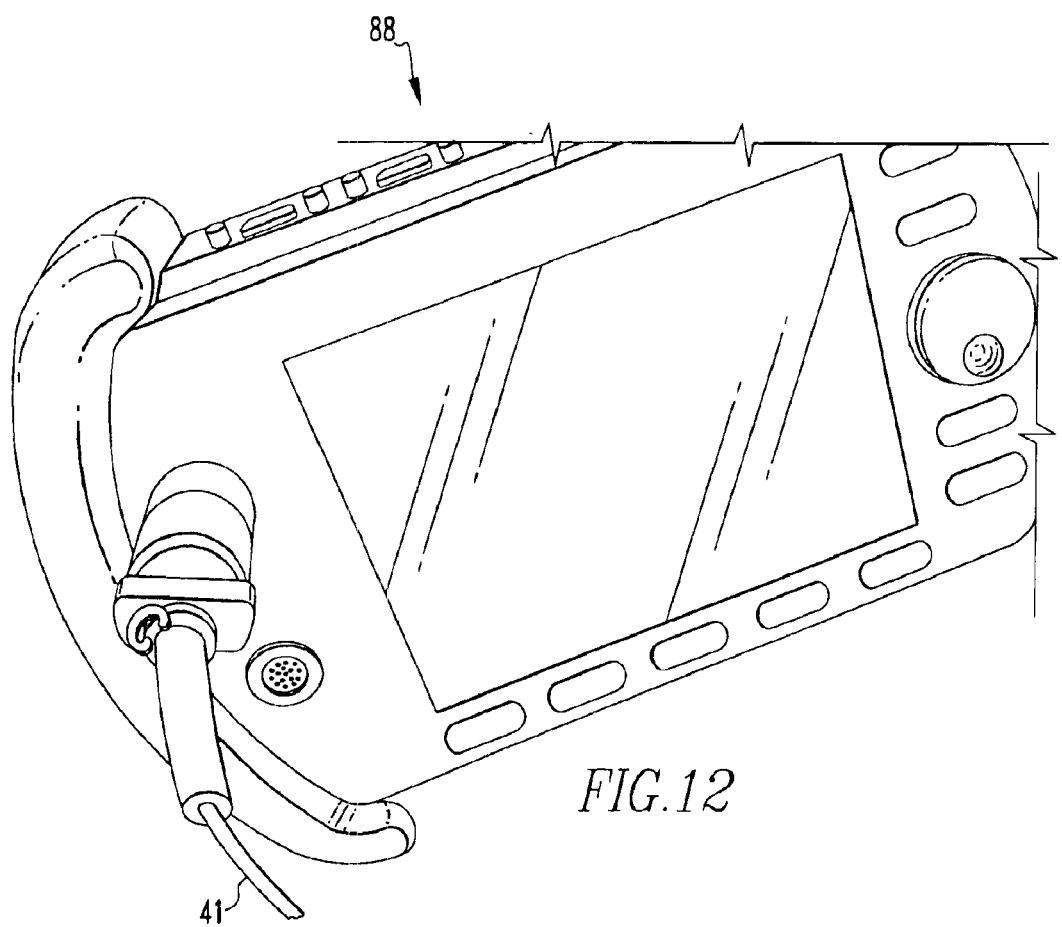
FIG. 12 is a front perspective view of a display screen for an eddy current probe according to the present invention.

Referring to FIG. 12, a display screen is illustrated. The display screen 88 provides a means for displaying and interpreting the results of the eddy current inspection. Preferred embodiments of the display screen 88 may toggle between an inductive screen and a video screen, but separate video and inductive display screens 88 may also be used.

To use the eddy current probe 10, the turning gear switch of the turbine is first locked out. Next, a conventional, well-known rotor positioning tool is connected to the rotor, so that the individual turbine blades may be rotated into close proximity with an inspection port. The appropriate inspection tip 14,16 and shaft extension 18,20,22 (if desired) are selected. The tip 14,16 may be connected either directly to the connector 30, or to an extension shaft 18,20,22 that is connected at its other end to the connector 30. The cable 41 is connected between the connection 40 and the display screen 88. The video probe 34 is inserted into the port 38.

The probe 10 is then inserted into the inspection port of a combustion turbine, and positioned in the appropriate location relative to a blade, using the lever 42 to control the angle of the probe 14,16 with respect to the shaft 24, and using the video probe 34 to monitor the probe tip's position. The tip 14,16 may then be moved across the surface of the blade while the inspector watches the display screen for differences in inductance indicating a defect. The inspector may remove the probe 10 to replace one probe tip 14,16 with another probe tip 14, 16, to inspect different portions of the blade, for example, switching from tip 14 to tip 16 when finished checking the flat surfaces, and beginning to inspect the edges.

Once a blade is inspected, the probe 10 is removed, and the rotor positioning tool is used to rotate the rotor so that the next blade is in close proximity to the inspection port. The process is repeated until all blades are inspected.

While specific embodiments of the invention have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the invention which is to be given the full breadth of the appended claims and any and all equivalents thereof.

What is claimed is:

1. An eddy current probe for inspecting multiple portions of a turbine blade having different geometric surfaces, comprising:
   a shaft having a hollow main body having a pair of ends, with a handle being rigidly secured at one end, and a probe tip connector being pivotally secured at the other end;
   means for controlling an angle between the main body and the probe tip from the handle;
   an eddy current signal cable extending through said main body, connecting the probe tip connector with another cable connector on said handle; and
   a plurality of eddy current probe tips, each tip adapted to be removably received by the probe tip connector and having a different geometric configuration to inspect a different geometric surface of the turbine blade.

2. The eddy current probe according to claim 1, wherein said eddy current probe tip includes:
   at least one coil; and
   a magnetically permeable nose pivotally mounted in front of the at least one coil, being dimensioned and configured to be placed in contact with material to be inspected.

3. The eddy current probe according to claim 2, wherein the probe tip connector is dimensioned and configured to receive one of a plurality of eddy current probe tips, the probe tips being selected from the group consisting of bullnose tip and grovenose tip.

4. The eddy current probe according to claim 1, further comprising at least one shaft extension dimensioned and configured to connect between the eddy current probe tip and the probe tip connector.

5. The eddy current probe according to claim 1, further comprising a port for a video probe dimensioned and configured to permit a video probe to pass from the handle, through the main body, to a position in close proximity with the probe tip connector.

6. The eddy current probe according to claim 1, wherein the means for controlling the angle between the probe tip connector and the main body include:
   a lever secured within the handle; and
   a semirigid or rigid member extending between the lever and the probe tip connector.

7. The eddy current probe according to claim 6, wherein the lever is slidably mounted within the handle.

8. The eddy current probe according to claim 6, wherein the semirigid or rigid member is a metal strip.

9. The eddy current probe according to claim 1, further comprising a display screen.

10. The eddy current probe according to claim 9, wherein the display screen provides both an inductive screen and a video screen.

11. The eddy current probe according to claim 1, wherein the probe is dimensioned and configured to facilitate locating the probe tip adjacent to substantially all surfaces of a blade of a combustion turbine when the probe tip is inserted through an inspection port defined within the combustion turbine, without disassembly of the turbine.

12. An eddy current probe kit for inspecting multiple portions of a turbine blade having different geometric surfaces, comprising:
    a shaft having a hollow main body with a pair of ends, a handle secured toward one end of the shaft, and a probe tip connector secured toward the other end of the shaft;
    an eddy current signal cable connecting the probe tip connector with another cable connector for outputting the eddy current signal to an output device; and
    a plurality of eddy current probe tips, each tip adapted to be received by the probe tip connector and having a different geometric configuration to inspect a different geometric surface of the turbine blade.

13. The eddy current probe kit according to claim 12, wherein said eddy current probe tip includes:
    at least one coil; and
    a magnetically permeable nose pivotally mounted in front of the at least one coil, being dimensioned and configured to be placed in contact with material to be inspected.

14. The eddy current probe kit according to claim 13, wherein the probe tip connector is dimensioned and configured to receive one of the plurality of eddy current probe tips, the probe tips being selected from the group consisting of bullnose tip and grovenose tip.

15. The eddy current probe kit according to claim 12, further comprising at least one shaft extension dimensioned and configured to connect between the eddy current probe tip and the probe tip connector.

16. The eddy current probe kit according to claim 12, further comprising a port for a video probe dimensioned and configured to permit a video probe to pass from the handle, through the main body, to a position in close proximity with the probe tip connector.

17. The eddy current probe according to claim 12, further comprising a display screen.

18. The eddy current probe kit according to claim 17, wherein the display screen provides both an inductive screen and a video screen.

19. The eddy current probe kit according to claim 12, wherein the probe is dimensioned and configured to facilitate locating the probe tip adjacent to substantially all surfaces of a blade of a combustion turbine when the probe tip is inserted through an inspection port defined within the combustion turbine, without disassembly of the turbine.

20. The eddy current probe kit according to claim 12, wherein the turbine blade is located in the turbine section of a turbine engine or the compressor section of the turbine engine, and the turbine blade is a rotational blade or a stationary blade.

\* \* \* \* \*